(12) United States Patent
Privat De Fortune et al.

(10) Patent No.: US 11,105,824 B2
(45) Date of Patent: Aug. 31, 2021

(54) FACILITY FOR HANDLING AND STORING BIOLOGICAL SAMPLES AT VERY LOW TEMPERATURES

(71) Applicant: IRELEC, Saint-Martin-d'Heres (FR)

(72) Inventors: Matthieu Privat De Fortune, Saint-Martin-d'Heres (FR); Gerard Marot, Montbonnot-Saint-Martin (FR); Aymeric Cunrath, Crolles (FR); Yohan Briand, Saint-Nicolas-de-Macherin (FR); Rattena Tang, Grenoble (FR)

(73) Assignee: IRELEC, Saint-Martin-D'Heres (FR)

( * ) Notice: Subject to any disclaimer, the term of this patent is extended or adjusted under 35 U.S.C. 154(b) by 293 days.

(21) Appl. No.: 16/302,487

(22) PCT Filed: May 15, 2017

(86) PCT No.: PCT/EP2017/061632
§ 371 (c)(1),
(2) Date: Nov. 16, 2018

(87) PCT Pub. No.: WO2017/198628
PCT Pub. Date: Nov. 23, 2017

(65) Prior Publication Data
US 2019/0277868 A1    Sep. 12, 2019

(30) Foreign Application Priority Data

May 17, 2016 (FR) ...................... 16 54373

(51) Int. Cl.
*G01N 35/00* (2006.01)
*B01L 3/00* (2006.01)
(Continued)

(52) U.S. Cl.
CPC ....... *G01N 35/0099* (2013.01); *A01N 1/0242* (2013.01); *B01L 3/508* (2013.01);
(Continued)

(58) Field of Classification Search
CPC ................. G01N 35/0099; G01N 1/42; G01N 2035/00435; G01N 2213/3103;
(Continued)

(56) References Cited

U.S. PATENT DOCUMENTS

2006/0257999 A1* 11/2006 Chang .................... C40B 60/06
435/289.1
2007/0123999 A1* 5/2007 Raghibizadeh ......... B01L 9/543
700/1
(Continued)

FOREIGN PATENT DOCUMENTS

CN    102269667 A    12/2011
CN    102356291 A    2/2012
(Continued)

OTHER PUBLICATIONS

International Search Report dated Jul. 20, 2017 in PCT/EP2017/061632 filed on May 15, 2017.
(Continued)

*Primary Examiner* — Jill A Warden
*Assistant Examiner* — John McGuirk
(74) *Attorney, Agent, or Firm* — Oblon, McClelland, Maier & Neustadt, L.L.P.

(57) ABSTRACT

The invention essentially consists in advantageously using and arranging at least one robot (8) relative to one or more storage recipients (4) and a transfer station (5) for transferring the containers to the unit in such a way as to take advantage of the flexibility of movement and grip offered by the arm or arms of the robot or robots and its/their gripping member, in order to automate all of the operations carried out manually by an operator in conventional biobanks.

16 Claims, 6 Drawing Sheets

(51) Int. Cl.
  *G01N 1/42* (2006.01)
  *A01N 1/02* (2006.01)
  *F25D 25/02* (2006.01)
  *A61B 10/00* (2006.01)

(52) U.S. Cl.
  CPC .......... *G01N 1/42* (2013.01); *G01N 35/00732* (2013.01); *A61B 10/0096* (2013.01); *F25D 25/02* (2013.01); *F25D 25/021* (2013.01); *F25D 25/024* (2013.01); *F25D 25/025* (2013.01); *F25D 25/028* (2013.01); *G01N 2035/00752* (2013.01)

(58) Field of Classification Search
  CPC . G01N 2035/00326; G01N 2035/0412; G01N 2035/0418; G01N 2035/042; G01N 2035/0422; G01N 35/00732; G01N 2035/00752; G01N 2035/0425; A01N 1/0242; A01N 1/0257; A01N 1/02; A01N 1/0252; A01N 1/0263; B01L 3/508; B01L 2300/021; A61B 10/0096; F25D 25/02; F25D 25/021; F25D 25/024; F25D 25/025; F25D 25/028; G07F 11/62
  See application file for complete search history.

(56) References Cited

U.S. PATENT DOCUMENTS

| | | | |
|---|---|---|---|
| 2010/0086440 A1* | 4/2010 | Fattinger | G01N 35/028 422/63 |
| 2012/0272500 A1* | 11/2012 | Reuteler | G01N 35/1095 29/428 |
| 2012/0283867 A1 | 11/2012 | Gelbman et al. | |
| 2012/0309297 A1 | 12/2012 | Bates et al. | |
| 2013/0011226 A1 | 1/2013 | Camenisch et al. | |
| 2016/0095309 A1 | 4/2016 | Reuteler | |
| 2018/0202908 A1* | 7/2018 | Croquette | G01N 35/02 |

FOREIGN PATENT DOCUMENTS

| | | | |
|---|---|---|---|
| EP | 1 012 515 | 6/2000 | |
| EP | 2 146 163 A2 | 1/2010 | |
| EP | 2 169 405 A2 | 3/2010 | |
| EP | 2 232 175 | 9/2010 | |
| EP | 2 492 663 A2 | 8/2012 | |
| JP | 2002-205804 A | 7/2002 | |
| KR | 10-2014-0099810 A | 8/2014 | |
| WO | WO-9101365 A1 * | 2/1991 | ........... G01N 35/028 |
| WO | WO 98/43592 A2 | 10/1998 | |
| WO | WO 2009/094071 A2 | 7/2009 | |
| WO | WO 2011/047710 A1 | 4/2011 | |
| WO | WO 2014/001184 A1 | 1/2014 | |
| WO | WO-2017081281 A1 * | 5/2017 | ............ G07F 11/165 |

OTHER PUBLICATIONS

Preliminary French Search Report dated Feb. 9, 2017 in French Application 16 54373 filed on May 17, 2016.
Combined Chinese Office Action and Search Report dated Dec. 2, 2020 in corresponding Chinese Patent Application No. 201780030889.X (with English Translation and English Translation of Category of Cited Documents), 17 pages.

* cited by examiner

FACILITY FOR HANDLING AND STORING BIOLOGICAL SAMPLES AT VERY LOW TEMPERATURES

TECHNICAL FIELD

The present invention relates to the field of installations usually called "biobanks", which allow the storage of biological samples at very low temperatures and notably under cryogenic conditions, thanks in particular to using liquid nitrogen as the cold source.

It relates more particularly to automated biobanks, that is to say ones in which the stored samples are handled without the intervention of an operative.

The invention aims more particularly to improve this type of biobank, notably by allowing the use of sample storage receptacles already commercially available.

Although described with reference to a preferred application using commercial cryogenic storage receptacles, the invention can be applied to all types of storage receptacle.

Moreover, although described with reference to a preferred application in which the biological samples are contained in conservation tubes, the invention may also be applied to any type of biological sample receptacle, notably blood sachets.

PRIOR ART

In conventional biobanks, the biological sample containers are stored in receptacles cooled by liquid nitrogen, typically in a temperature range from −150° C. to −200° C., and handling them, that is to say loading/unloading a receptacle, is done manually by an operative. The advantages of such biobanks are the minimum investment cost, flexibility of use requiring little maintenance.

However, they have major disadvantages, including management of the samples, which is effected by manual definition with the attendant risks of handling errors, the traceability of the samples which is not 100% certain and, finally, for the operatives, the risks of anoxia linked to the cryogenic environment (presence of liquid nitrogen), the poor ergonomics and the force needed to lift the stored items from a storage receptacle (high weight, phenomenon of adhesion caused by the cold).

Various attempts have already been made to automate biobanks.

There may be cited the patent applications WO2014001184 A1, EP2232175 A2, CN102269667 A, US2012309297 A1, JP2002205804 A, and EP1012515 A1, which disclose automated biobank solutions.

Although automation brings substantial advantages such as guaranteeing tracing of samples by means of databases, safety of operatives and handling operations, the automated biobanks already proposed have major disadvantages.

First of all, they necessitate a very high investment on purchase and in operation and maintenance, because of a bespoke design for each configuration, notably with the impossibility of reusing existing standard equipment, such as standard storage receptacles.

Then, their design means that their temperature range is restricted, with reaching cryogenic temperatures typically less than −150° C. being impossible in many cases.

Finally, as mentioned, their bespoke design means that they are dedicated to one and only one configuration, which does not allow them to evolve.

There is therefore a need to improve installations for handling and storing biological samples, or biobanks, notably by circumventing the disadvantages both of conventional biobanks in which the samples are handled manually and the automated biobanks already proposed.

The object of the invention is to respond at least in part to this need.

SUMMARY OF THE INVENTION

To this end, the invention concerns an installation for handling and storing biological samples at very low temperatures, notably under cryogenic conditions, comprising:
a plurality of storage boxes with multiple compartments, each compartment being adapted to house a container each adapted to contain one or more biological samples;
a plurality of storage columns, each extending along a longitudinal axis and divided into a plurality of storage drawers, termed racks, each adapted to receive by translation transversely to the longitudinal axis one of the plurality of boxes;
at least one storage receptacle, with thermal insulation, the interior of which is adapted to be subjected to very low temperatures, comprising in its upper part a cellular grid in which each cell is adapted to receive vertically one of the plurality of columns;
a transfer station comprising a transfer table on which an operative can place one or more boxes with multiple compartments, termed transfer boxes, each compartment of which is also adapted to house one of a plurality of containers each adapted to contain one or more biological samples;
a station for loading/unloading the storage boxes one by one, comprising a table, termed a waiting table, at least one extraction means for extracting any of the storage boxes, from a rack of a column position in said station, and moving it to a position placed on the waiting table, and at least one pusher means for pushing a box, from its position placed on the waiting table, into an empty rack of a column positioned in said station;
a station for loading/unloading the containers one by one, comprising a table, termed a handling table, adapted to support at least two boxes with compartments, one of which is the transfer box and the other of which is a selected one of the storage boxes;
at least one robot comprising a gripping member adapted to grip the upper end of a storage column, or of a storage box, or of a container, the robot(s) being adapted to enable movement of the gripping member or members with six degrees of freedom.

According to the invention the installation is configured so that the gripping member of the robot can simultaneously:
i/ move the transfer box from the transfer table onto the handling table,
ii/ extract any of the columns from one of the cells of the grid of the storage receptacle and then move it into the station for loading/unloading the boxes in a position such that the extraction means can extract a selected storage box on the waiting table,
iii/ move the selected storage box from the waiting table onto the handling table,
iv/ extract any of the receptacles one by one from one of the compartments of the selected storage box, positioned on the handling table and move it into one of the compartments of the transfer box,
and vice versa with the pusher means to push a selected storage box into an empty rack of a column positioned in the station for loading/unloading the boxes.

Here the expression "vice versa" means that the steps i/ to iv/ executed by the six-axis robot and its gripping member are carried out in the opposite loading/unloading direction to the transfer, only the pusher means operating instead and in place of the extraction means (step ii).

In the framework of the invention, steps i/ iv/ can be implemented by a single gripping member or several types of gripping members, which are changed according to one or the other of steps i/ to iv/.

By "very low temperatures" is meant here and in the context of the invention temperatures less than −100° C., preferably less than −150° C.

According to one advantageous embodiment, the installation comprises a single robot with six degrees of freedom of movement, termed a six-axis robot.

Accordingly, the invention essentially consists in using and carefully arranging at least one robot, with six axes of movement relative to one or more storage receptacles and a station for transferring containers one by one so as to exploit the flexibility of movement and of gripping offered by the arm(s) of the robot(s) and its (their) gripping member in order to automate all of the operations effected manually by an operative in classic biobanks.

Accordingly, the arm(s) of the robot(s) with its (their) gripping member effect(s) on its (their) own only the operations that are usually carried out manually in prior art biobanks. These operations may be summarized as follows:
- extraction and insertion of storage boxes from and in the transfer station;
- extraction and insertion of storage columns from and in the storage receptacles;
- extraction and insertion of storage boxes from and in the columns;
- extraction and insertion of biological sample containers from and in the boxes.

Surprisingly, although numerous attempts to automate biobanks have already been carried out in the past, none has conceived of exploiting the flexibility of movement offered by the arm of a six-axis robot and its gripping member.

The numerous advantages of the installation according to the invention include:
- the lower cost than prior art automated biobanks which are necessarily bespoke while retaining their inherent advantages namely automation, safety and traceability of samples (barcode reading, database, etc.), safety of operatives;
- the possibility of installing all the components of the installation in a controlled environment enclosure, which guarantees the integrity of the samples (temperature, frost, etc.);
- the possible reuse of storage receptacles existing in conventional biobanks, notably receptacles operating under cryogenic conditions;
- the modular layout, with in particular the possibility of employing more or fewer storage receptacles, moving the robot on a rail to have access to a very large number of aligned storage receptacles.
- the possibility of being able to continue the operation of the installation manually, which makes it possible to ensure continuous operation whilst facilitating maintenance operations, and to preserve some flexibility.
- the possibility of evolution of the installation;
- the ease and speed of automation of a conventional biobank already in use.

According to one advantageous embodiment, the installation comprises a controlled environment enclosure providing safe access to the transfer station for an operative from the exterior, the enclosure being configured to house the plurality of storage boxes, the plurality of storage columns, the storage receptacle(s), the transfer station, the loading/unloading stations and the six-axis robot.

Access to the transfer station may consist in an airtight airlock or in an airtight drawer.

In order to guarantee traceability, each storage column and/or each storage box and/or the transfer box may advantageously comprise a means, preferably a (one- or two-dimensional) barcode, of identification by an identification reader carried by the robot.

Thanks to the robot's flexibility of movement and of gripping, multiple configurations of the layout of the installation may be envisaged, notably the following advantageous configurations:
- a plurality of storage receptacles arranged substantially to form a portion of a circle with the robot fixed and arranged within the circle portion, the station for loading/unloading the boxes one by one being arranged inside the circle, the station for loading/unloading the containers one by one being arranged on the circle;
- a plurality of storage receptacles arranged substantially to form at least one row, with the robot mounted on a carriage mobile on a rail along the row.

According to one advantageous variant, the storage receptacle or receptacles each comprise a lid for closing the receptacle not involved in the storage configuration in the extraction from it or reciprocally the insertion in it of a column.

According to this variant, the control and command unit of the robot is preferably adapted to command the opening and reciprocally the closing of each storage receptacle.

There may advantageously be provided one or more cylinders, as extraction means and/or pusher means of the boxes of a column when it is positioned on the waiting table.

According to an advantageous variant, there may be provided as extraction means a plurality of cylinders each positioned facing a rack of a storage column, when it is positioned on the handling table.

The gripping member of the robot may also constitute the pusher means instead and in place of the cylinder(s).

The storage and transfer boxes are advantageously adapted to house conservation tubes or flexible envelopes, such as blood sachets as biological sample containers.

The storage boxes may each comprise a lid, the handling member of the robot then being adapted to remove a lid from its box before the one by one extraction of the containers housed in said box, and vice versa.

The storage receptacle or receptacles preferably operate under cryogenic conditions, notably using liquid nitrogen as the cold source.

According to one advantageous embodiment, the station for loading/unloading receptacles one by one is configured as a controlled atmosphere insulated enclosure at very low temperatures. This enables effective protection against frost by a dry atmosphere and keeping the biological samples cold.

The invention also consists in use of the installation described above for storing biological samples under cryogenic conditions in a controlled environment enclosure.

DETAILED DESCRIPTION

Other advantages and features of the invention will emerge more clearly on reading the detailed description of embodiments of the invention given by way of nonlimiting illustration with reference to the following figures, in which.

It is here specified that throughout the present application, the terms "lower", "central", "higher", "above", "below", "interior", "exterior", are to be understood with reference to a storage receptacle and a storage column of the installation according to the invention arranged vertically.

Figure 1:
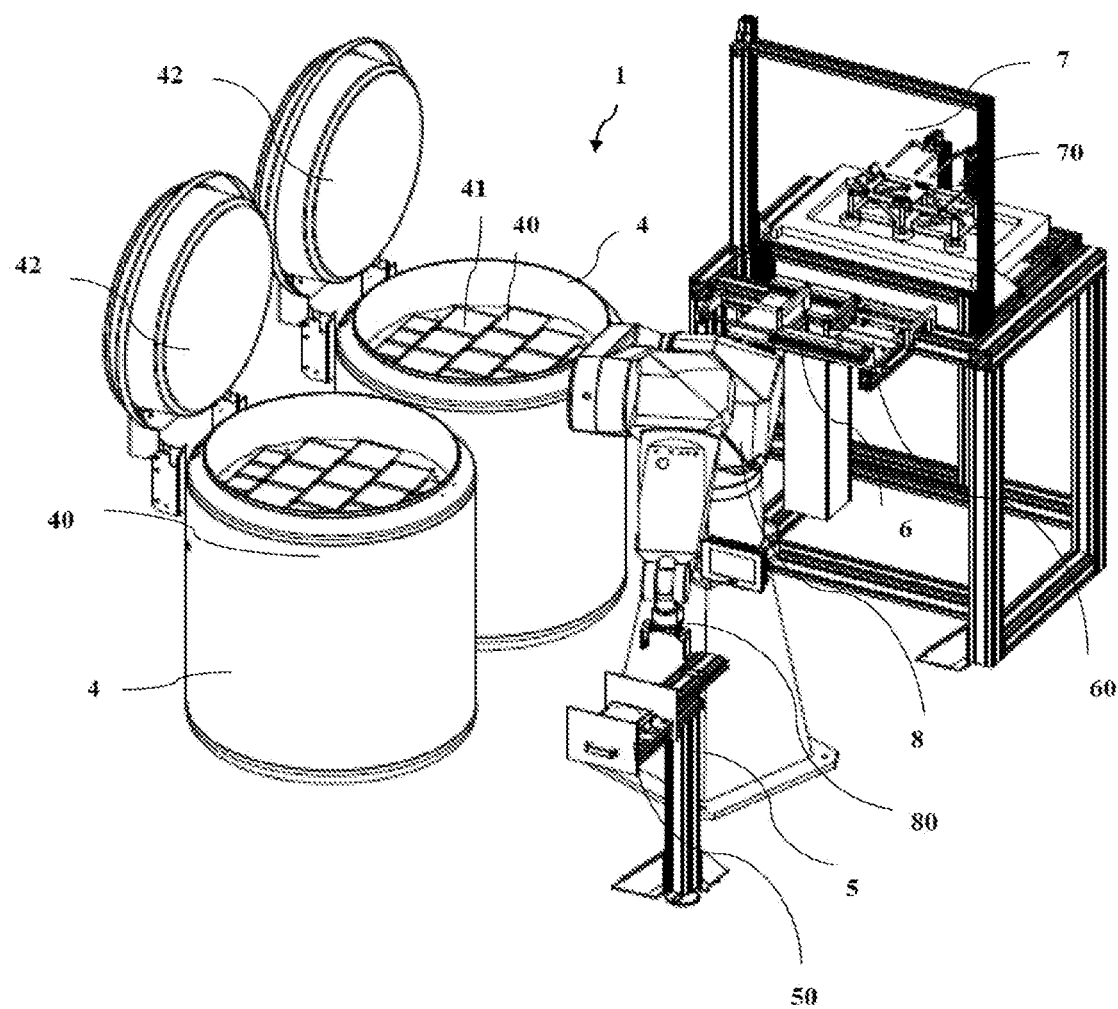
FIG. 1 is a perspective view of one example of one part of an installation according to the invention for handling and storing biological samples.
Figure 1A:
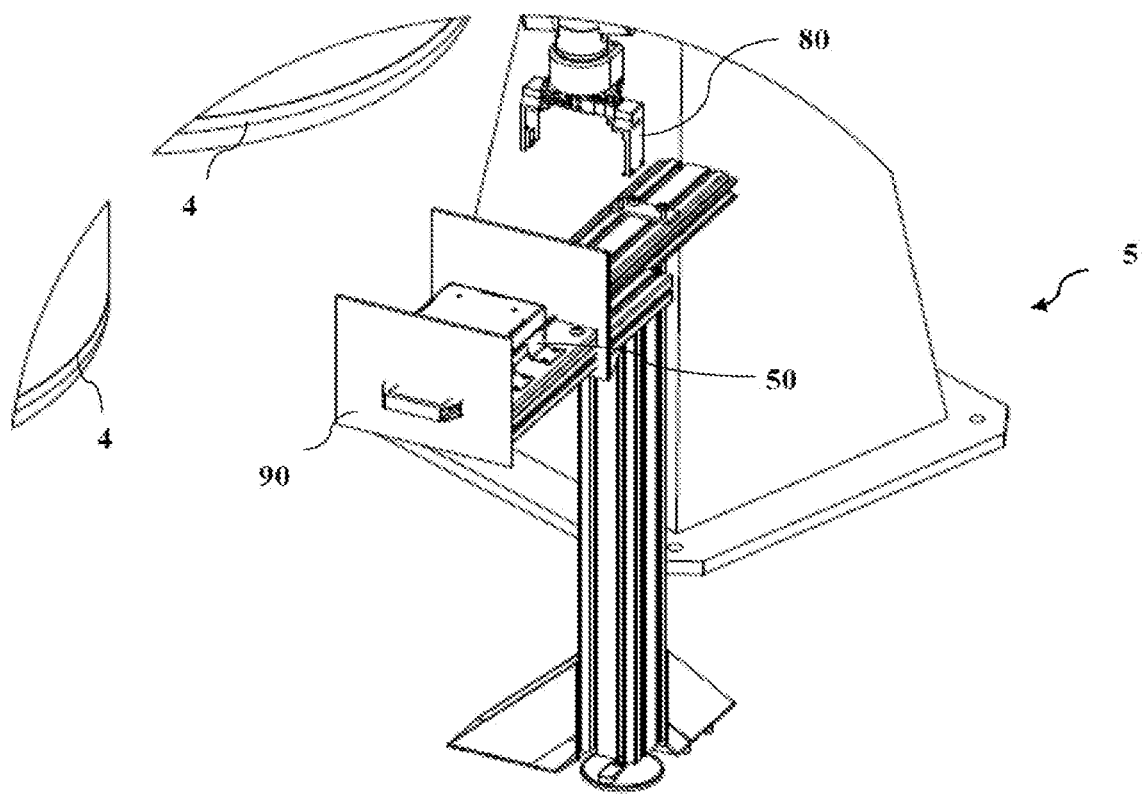
FIG. 1A is a detail view in perspective of FIG. 1 showing the transfer station from outside the installation.
Figure 2:
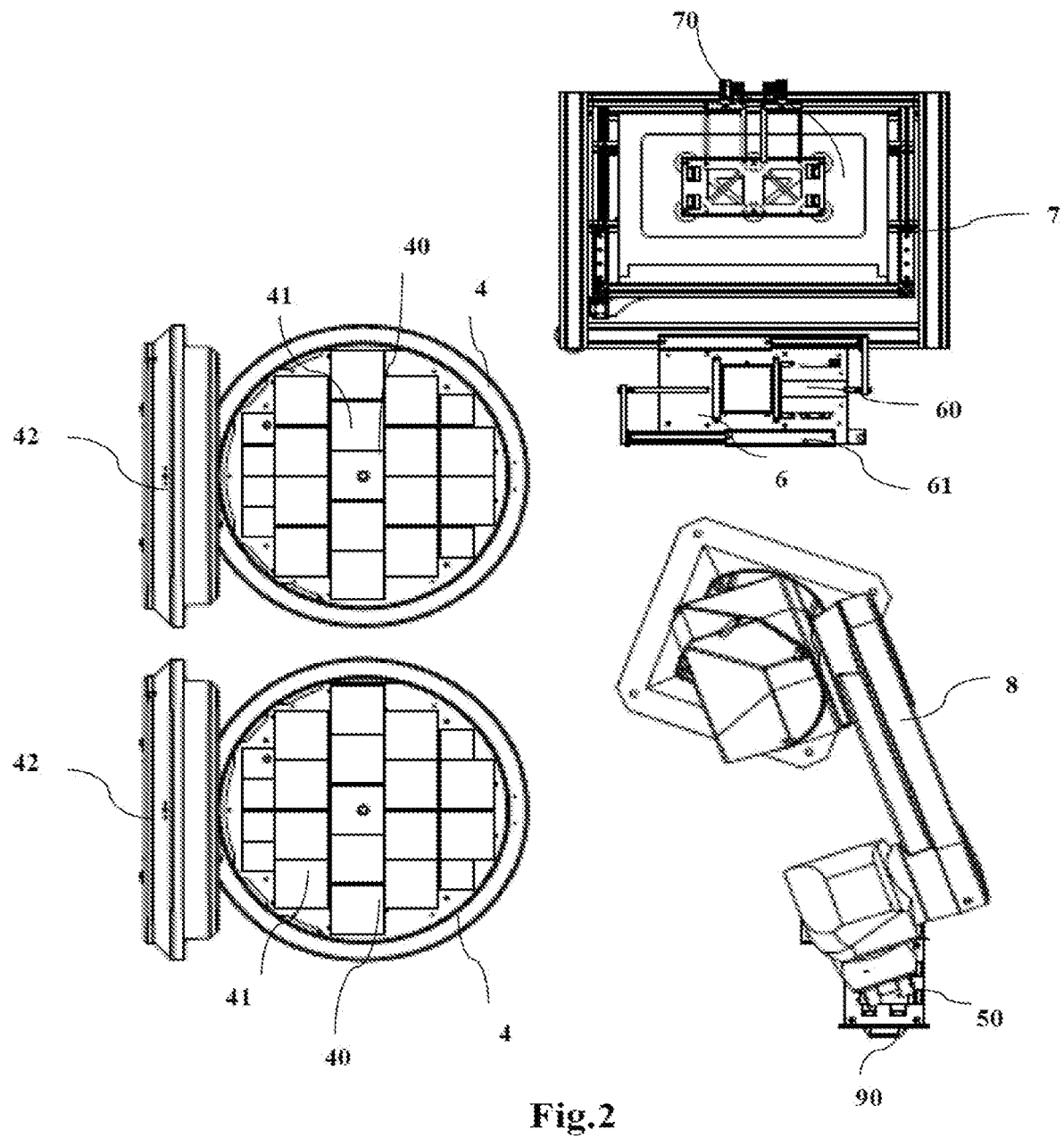
FIG. 2 is a plan view of FIG. 1.

There are shown in FIGS. 1 and 2 all of the essential components of an installation 1 according to the invention for handling and storing biological samples at very low temperatures, notably under cryogenic conditions.

The biological samples are contained in containers.

Figure 6:
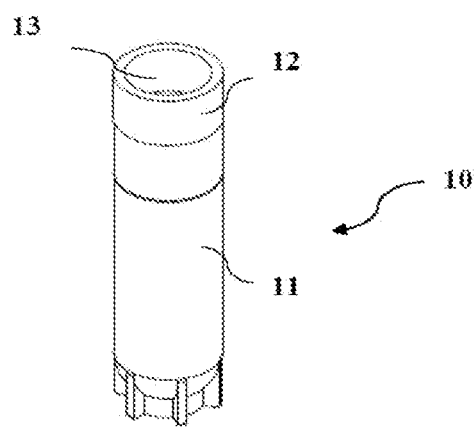
FIG. 6 is a perspective view of a biological sample conservation tube suitable as a receptacle suitable for the installation according to the invention.

In the example shown, the sample containers 10 used are conservation tubes as already used. A conservation tube 10 is shown in FIG. 6: it comprises a blind tube part 11 to which is removably fixed a stopper 12 with a hollow interior 13.

Figure 5:
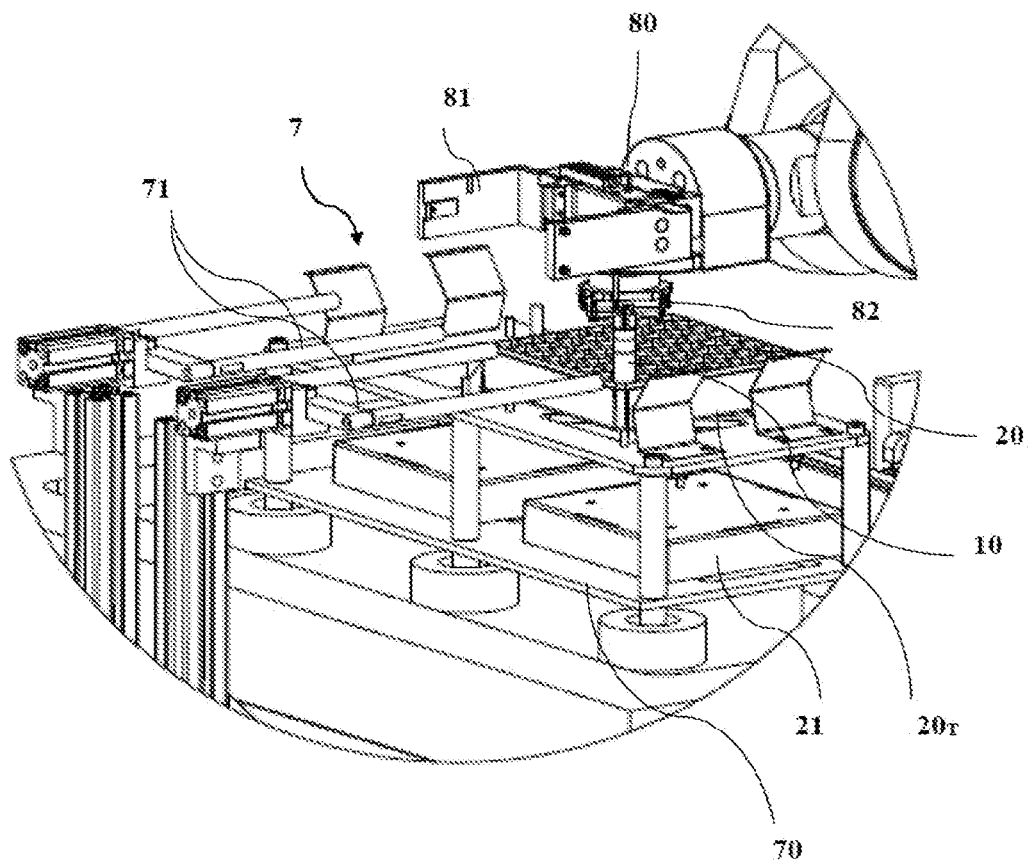
FIG. 5 is a perspective view of a station for loading/unloading sample receptacles one by one of the installation according to the invention.

A plurality of tubes 10 are individually housed in the compartment 20 of a storage box 2 with multiple compartments. A tube 10 housed in a compartment 20 is shown in FIG. 5. In this FIG. 5 there is further seen a box 2 lid 21 that is removed from the latter in order to enable the extraction or the insertion of the tubes 10 one by one from and into the compartments 20 of the box 2.

Figure 3:
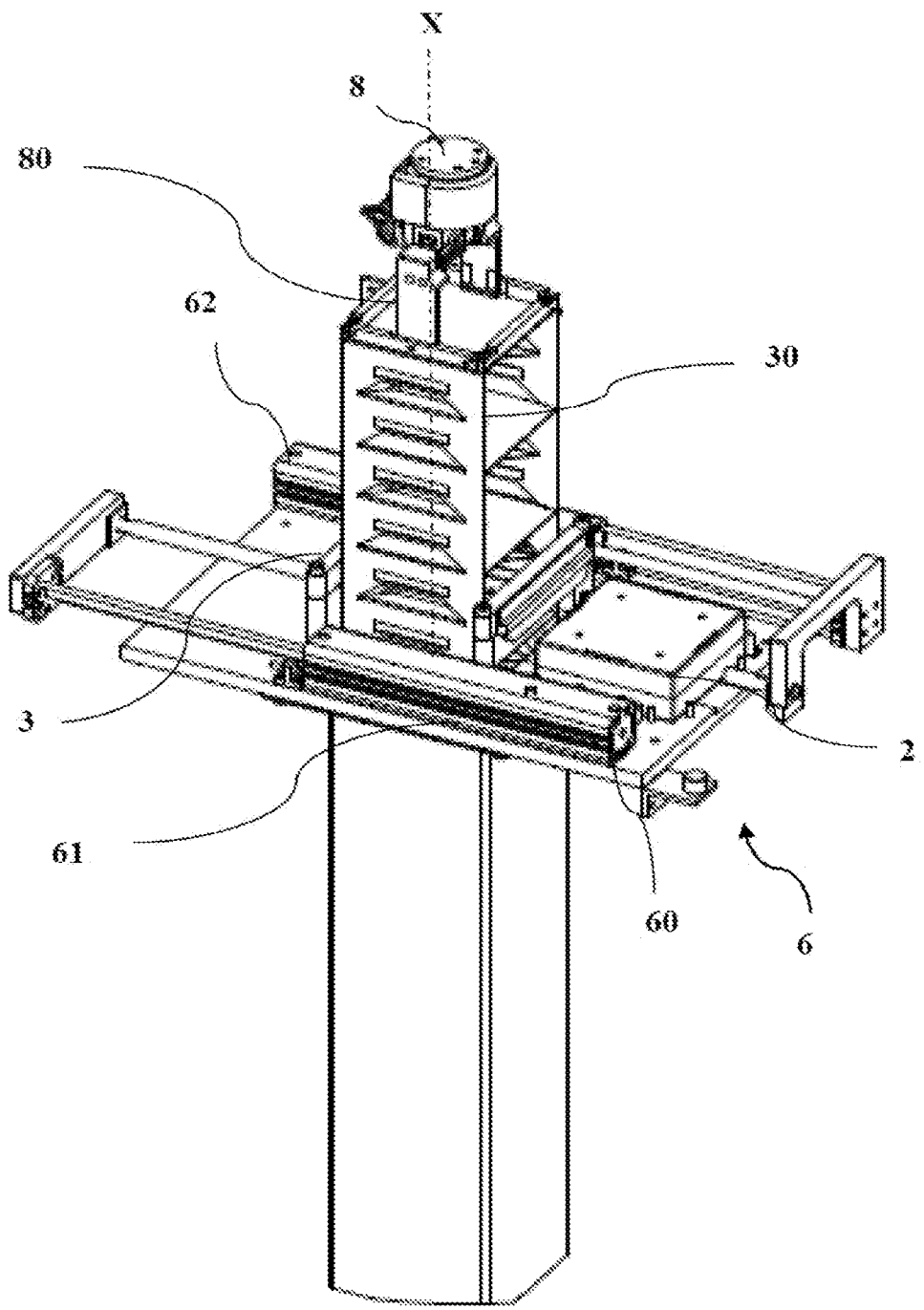
FIG. 3 is a perspective view showing the station of the installation according to the invention for loading/unloading storage boxes one by one, with a box storage column in position in the station.

The installation 1 comprises storage columns 3 with drawers or racks. As shown in FIG. 3, a storage column 3 extends along a longitudinal axis X and is divided into a plurality of storage racks 30. Each rack 30 can receive a storage box 2 by translation transverse to the longitudinal axis X.

Two identical storage receptacles 4 are provided, with thermal insulation, the interior of which is adapted to be subjected to very low temperatures, notably when liquid nitrogen is used as the cold source. The receptacle can be of the double-wall type in which a vacuum guarantees thermal insulation from the exterior. The receptacles 4 are preferably fixed to the floor.

Each receptacle 4 comprises in its upper part a cellular grid 40 each cell 41 of which can receive vertically a storage column 3. Each receptacle 4 is closed by a removable lid 42.

The installation 1 according to the invention includes a controlled environment enclosure, not shown, in which all the essential components are housed.

To transfer storage boxes 2 one by one from the exterior of the enclosure, a transfer station 5 is installed comprising a transfer table 50 which an operative can access and move thereto a transfer box 2T with compartments 20 identical to those of the other boxes. Access is preferably via a controlled atmosphere insulated drawer or airlock system enabling the safety of the operative to be guaranteed.

The installation also comprises a station 6 for loading/unloading boxes 2 one by one, which is an intermediate station between the storage receptacles 4 and a station 7 for loading/unloading the containers one by one.

As shown in FIG. 3, the station 6 includes a waiting table 60 with a cylinder 61 or 62 on each of its longitudinal edges. One cylinder 61 enables any of the storage boxes 2 to be extracted from a rack 30 of a column 3 positioned in said station 6 and moved to a position placed on the waiting table 60. The other cylinder 62 enables a box 2 to be pushed from its position placed on the waiting table 60 into an empty rack 30 of a column 3 positioned in said station 6.

To load/unload 7 sample tubes 10 one by one, a station 7 is arranged in the vicinity of the station 6. As shown in FIG. 5, this station 7 comprises a handling table 70, adapted to support at least two boxes 2, one of which is the transfer box $2_T$ and the other of which is a selected one of the storage boxes. This station 7 is advantageously configured in a controlled cold environment.

Finally, at the center of the installation 1, a six-axis robot 8 fixed to the floor includes an arm on which is mounted a gripping member 80, 81, 82. The latter is adapted to grip the upper end of a storage column 3, or of a storage box 2, or of a sample tube 10.

Figure 4:
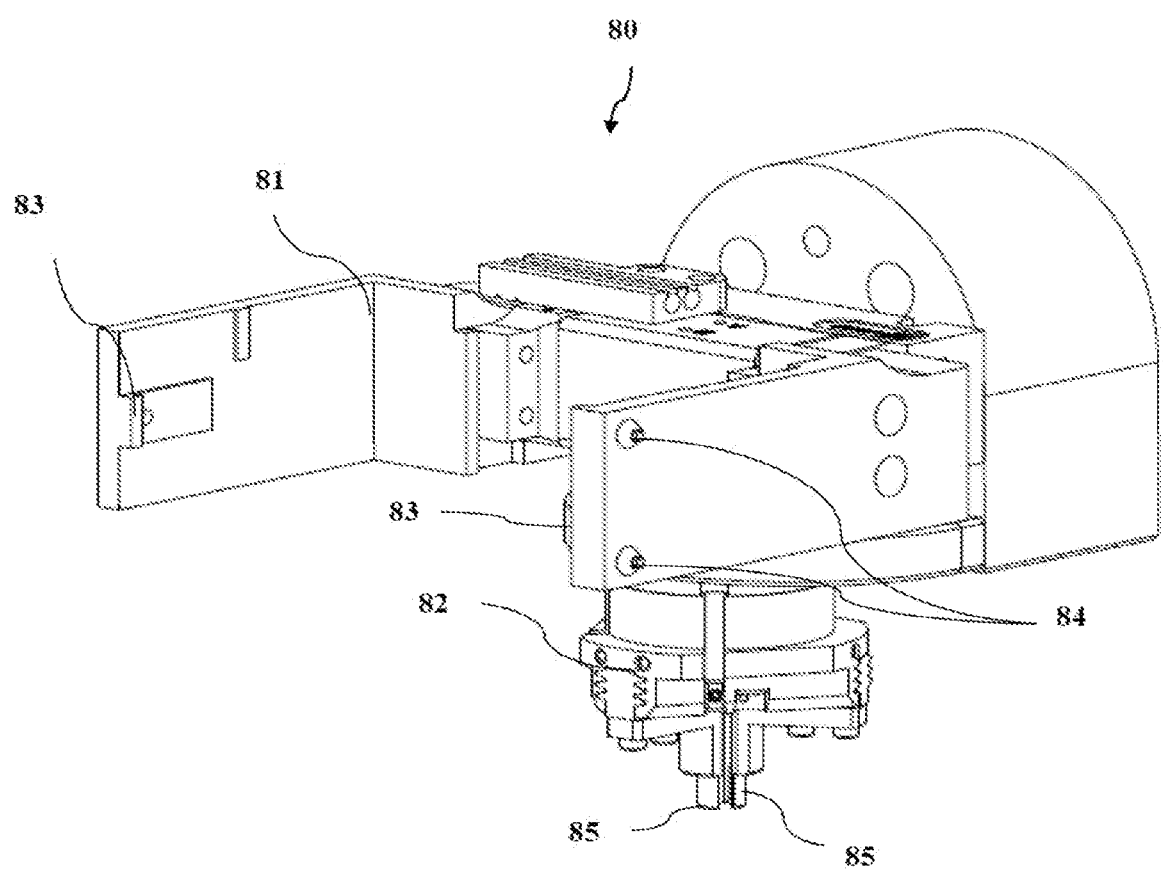
FIG. 4 is a perspective view showing the gripping member of the six-axis robot of the installation according to the invention.

The gripping member 80 is shown in detail in FIG. 4: it comprises a clamp 81 with two branches mobile relative to one another and an element 82 for gripping the tubes 10 one by one fixedly mounted at 90° to the axis of the clamp 81.

The clamp 81 carries on the inside of each of its branches a gripping wedge 83 and on the outside of each of its branches gripping lugs 84.

For its part, the gripping element 82 comprises one or more gripping fingers 85, advantageously three concentric figures disposed at 120° to one another.

The gripping member operates as follows:
- to grip a storage column 3, the branches of the clamp 81 are moved away from one another, and the gripping lugs 84 then come to be locked into corresponding recesses in the upper part of the column;
- to grip a box 2, the branches of the clamp 81 are moved toward one another, and the gripping wedges 83 then come to bear against the bottom of the box while the branches come to bear on the lateral sides of the box;
- to grip a tube 10, the fingers 85 are moved towards one another and inserted in the recess 13 of the stopper 12 of the tube and are then moved away from one another so as to be locked onto the stopper 12.

The various steps in the operation of the installation 1 according to the invention are described now, executed by a control and command unit of the robot 8 and the storage receptacles 4, respectively for an operation of withdrawing one or more sample tubes from storage to the exterior of the enclosure of the installation and conversely for depositing one or more sample tubes in a storage receptacle from the exterior of the enclosure.

1/ Withdrawal

Using a human-machine interface, an operative selects withdrawal of a sample tube 10.

The control unit then verifies in its database that the column 3 and the storage box 2 and the selected sample tube 10 are present.

If the response is positive, the operative then places in the access airtight drawer or airlock 90 a transfer box $2_T$ with at least one empty compartment 20.

Via the control and command unit and its gripping member 80 the robot 8 then carries out the following successive steps:

positioning the transfer box $2_T$ on the handling table 70 of the station 7 for loading/unloading tubes one by one;

opening the lid 42 of one of the storage receptacles 4;

gripping a storage column 3 with the clamp 81 and then extracting it from the storage receptacle 4;

placing the storage column 3 held by the clamp 81 on the loading/unloading station 6;

if necessary, reading the identification means of the column 3 that has been placed, typically by reading a barcode;

extracting the selected box 2 from the column 3 by the extractor cylinder 61 to a position on the waiting table 60 accessible by the clamp 81, the column 3 being still held by the clamp 81;

if necessary, reading the identification means of the selected box 2, typically by reading a barcode;

stowing the storage column 3 in the receptacle 4;

closing the receptacle 4;

positioning the selected box 2 on the handling table 70;

if necessary, gripping the lids 21 of the transfer box $2_T$ and of the selected box 2 by means of the clamp 81 and then positioning them in the station 7;

gripping one or more sample tubes 10 in the selected box 2 by means of the gripping element 82 of the clamp, and positioning same in the transfer box $2_T$;

if necessary, reading the identification means of the selected sample tube or tubes 10, typically by reading a barcode;

if necessary, gripping of the lids 21 in their position in the station 7 and repositioning them on the bottom of the transfer box $2_T$ and of the selected storage box 2;

gripping the selected box 2 by means of the clamp 81 in its position on the handling table 70 and positioning it on the waiting table 70;

opening the lid 42 of one of the storage receptacles 4;

gripping a storage column 3 by means of the clamp 81 and then extracting it from the storage receptacle 4;

reinserting said box 2 in the column 3 by means of the pusher cylinder 62;

if necessary, gripping another selected box in another column of the same receptacle 4 or another receptacle and transferring other sample tubes contained in the other box;

closing the lid 42 of the receptacle 4.

The operative then recovers the transfer box $2_T$ filled with the selected sample tube or tubes 10 from the access to the transfer station 5.

2/ Storage

Via the human-machine interface, an operative selects deposition of a sample tube 10.

The control unit then verifies in its database that locations are available in a column 3 and in a storage box 2.

If the response is positive, the operative then places in the access airtight drawer or airlock 90 a transfer box $2_T$ with at least one empty compartment 20.

Via the control and command unit, using its gripping member 80 the robot 8 then effects the following successive steps:

placing the transfer box $2_T$ on the handling table 70 of the station 7 for loading/unloading the tubes one by one;

opening the lid 42 of one of the storage containers 4;

gripping a storage column 3 by means of the clamp 81 and then extracting it from the storage receptacle 4;

placing the storage column 3 held by the clamp 81 on the loading/unloading station 6;

if necessary, reading the identification means of the placed column 3, typically by reading a barcode;

extracting the selected box 2 with free compartment(s) 20 from the column 3 by means of the extractor cylinder 61 to a position on the waiting table 60 accessible by the clamp 81, the column 3 still being held by the clamp 81;

if necessary, reading the identification means of the selected box 2, typically by reading a barcode;

stowing the storage column 3 in the receptacle 4;

closing the receptacle 4;

placing the selected box 2 on the handling table 70;

if necessary, gripping the lids 21 of the transfer box 2T and of the selected storage box 2 by means of the clamp 81 and then placing them in the station 7;

handling one or more sampling tubes 10 from the transfer box $2_T$ by means of the handling element 82 of the clamp, and placing same in the selected box 2;

if necessary, reading the identification means of the selected sample tube or tubes 10, typically by reading a barcode;

if necessary, gripping the lids 21 in their position in the station 7 and repositioning them on the bottom of the transfer box $2_T$ and of the selected storage box 2;

gripping the selected box 2 by means of the clamp 81 in its position on the handling table 70 and placing it on the waiting table 70;

opening the lid 42 of one of the storage receptacles 4;

gripping a storage column 3 by means of the clamp 81 and then extracting it from the storage receptacle 4;

reinserting said box 2 in the column 3 by means of the pusher cylinder 62;

if necessary, gripping another box in the same column and transferring new samples, if necessary, gripping another selected box in the same column and transferring other sample tubes 10 contained in the other box;

gripping the storage column 3 by means of the clamp 81 and then reinserting it inside the storage receptacle 4;

if necessary, gripping another column from the same receptacle or from another receptacle and transferring other sample tubes 10 contained in the other box;

closing the lid 42 of the receptacle 4.

The operative then recovers the empty transfer box $2_T$ from the access to the transfer station 5.

Generally speaking, the installation according to the invention can be used for handling and storing biological samples at very low temperatures contained in diverse and varied containers.

Other variants and advantages of the invention can be obtained without this departing from the scope of the invention.

In particular, although in the embodiment shown there is a single six-axis robot 8, two robots may very well be envisaged, each with three degrees of freedom and independent of the other robot.

The invention is not limited to the examples that have just been described; notably features from the examples shown may be combined with one another in variants that are not shown.

The invention claimed is:

1. An installation for handling and storing biological samples at very low temperatures, comprising:

a plurality of storage boxes with multiple compartments, each compartment being adapted to house a container each adapted to contain one or more biological samples;

a plurality of storage columns, each extending along a longitudinal axis and divided into a plurality of racks, each adapted to receive by translation transversely to the longitudinal axis one of the plurality of boxes;

at least one storage receptacle, with thermal insulation, the interior of which is adapted to be subjected to very low temperatures, comprising in its upper part a cellular grid in which each cell is adapted to receive vertically one of the plurality of columns;

a transfer station comprising a transfer table on which an operative can place one or more transfer boxes with multiple compartments, each compartment of which is also adapted to house one of a plurality of containers each adapted to contain one or more biological samples;

a station for loading/unloading the storage boxes one by one, comprising a waiting table, at least one extraction means for extracting any of the storage boxes, from a rack of a column position in said station, and moving it to a position placed on the waiting table, and at least one pusher means for pushing a box, from its position placed on the waiting table, into an empty rack of a column positioned in said station;

a station for loading/unloading the containers one by one, comprising a handling table, adapted to support at least two boxes with compartments, one of which is a selected one of the transfer boxes and the other of which is a selected one of the storage boxes;

a single robot with six degrees of freedom of movement comprising a gripping member adapted to grip the upper end of a storage column, or of a storage box, or of a container, the at least one robot being adapted to enable movement of the gripping member with six degrees of freedom the installation being configured so that the gripping member of the robot can:

i) move the selected transfer box from the transfer table onto the handling table, ii) extract any of the columns from one of the cells of the grid of the storage receptacle and then move it into the station for loading/unloading the boxes in a position such that the extraction means can extract a selected storage box on the waiting table, iii) move the selected storage box from the waiting table onto the handling table, and iv) extract any of the containers one by one from one of the compartments of the selected storage box, positioned on the handling table and move it into one of the compartments of the selected transfer box, and vice versa with the pusher means to push a selected storage box into an empty rack of a column positioned in the station for loading/unloading the boxes.

2. The installation as claimed in claim 1, comprising a controlled environment enclosure providing safe access to the transfer station for an operative from the exterior, the enclosure being configured to house the plurality of storage boxes, the plurality of storage columns, the storage receptacle(s), the transfer station, the loading/unloading stations and the robot.

3. The installation as claimed in claim 2, the access to the transfer station consisting of an airtight airlock or in an airtight drawer.

4. The installation as claimed in claim 1, wherein each storage column and/or each storage box and/or the transfer box comprises a barcode for identification by an identification reader carried by the robot.

5. The installation as claimed in claim 1, comprising a plurality of storage receptacles arranged substantially to form a portion of a circle with the robot fixed and arranged within the circle portion, the station for loading/unloading the boxes one by one being arranged inside the circle, the station for loading/unloading the containers one by one being arranged on the circle.

6. The installation as claimed in claim 1, comprising a plurality of storage receptacles arranged substantially to form at least one row with the robot mounted on a carriage mobile on a rail along the row.

7. The installation as claimed in claim 1, the storage receptacle or receptacles each comprising a lid for closing the receptacle, not involved in the storage configuration in the extraction from it or reciprocally in the insertion in it of a column.

8. The installation as claimed in claim 7, wherein a control and command unit of the robot are adapted to command the opening and reciprocally the closing of each storage receptacle.

9. The installation as claimed in claim 1, comprising one or more cylinders, as extraction means and/or pusher means.

10. The installation as claimed in claim 9, comprising as extraction means a plurality of cylinders each positioned facing a rack of a storage column when it is positioned on the waiting table.

11. The installation as claimed in claim 9, wherein the gripping member of the robot constitutes the pusher means.

12. The installation as claimed in claim 1, wherein the storage and transfer boxes are adapted to house conservation tubes or flexible envelopes.

13. The installation as claimed in claim 1, wherein the storage boxes each comprises a lid, the gripping member of the robot then being adapted to remove a lid from its box before the one by one extraction of the containers housed in said box, and to move the lid back on the box after the one by one extraction of the containers housed in said box.

14. The installation as claimed in claim 1, wherein the storage receptacle or receptacles operate(s) under temperatures under −150° C.

15. The installation as claimed in claim 1, wherein the station for loading/unloading the containers one by one is configured as an airtight enclosure with an environment at very low temperatures.

16. The installation as claimed in claim 1, wherein the installation is configured to store biological samples under cryogenic conditions in controlled environment receptacles.

* * * * *